United States Patent [19]
Spinelli et al.

[11] Patent Number: 5,506,232
[45] Date of Patent: Apr. 9, 1996

[54] 6,9-BIS[(2-AMINOETHYL)AMINO]BENZO[G]ISOQUINOLINE-5,10-DIONE AND ITS DIMALEATE SALT

[75] Inventors: Silvano Spinelli, Monza; Roberto DiDomenico, Milan, both of Italy

[73] Assignee: Boehringer Mannheim Italia S.p.A., Monza, Italy

[21] Appl. No.: 220,007

[22] Filed: Mar. 28, 1994

[51] Int. Cl.⁶ .......................... C07D 419/14; A61K 31/47
[52] U.S. Cl. ............................................ 514/290; 546/101
[58] Field of Search ............................. 546/101; 514/290

[56] References Cited

FOREIGN PATENT DOCUMENTS

WO92/15300  9/1992  WIPO.

OTHER PUBLICATIONS

Krapcho et al, J. Med. Chem, vol. 28, pp. 1124–1126, 1985.

Krapcho et al., J. Med Chem, vol. 37, pp. 828–837, 1994.

*Primary Examiner*—Alan L. Rotman
*Assistant Examiner*—Zinna N. Davis
*Attorney, Agent, or Firm*—Nikaido, Marmelstein, Murray & Oram

[57]  ABSTRACT

In the search for novel heteroanalogs of anthracendiones, 6,9-bis[(2-aminoethyl)amino]benzo[g]isoquinoline-5,10-dione dimaleate salt (BBR 2778), was selected as the most promising compound. New methods of synthesis produce the compound in purity greater than 99%.

5 Claims, 4 Drawing Sheets

6,9-BIS[(2-AMINOETHYL)AMINO] BENZO[G] ISOQUINOLINE-5,10-DIONE AND ITS DIMALEATE SALT

BACKGROUND

Field of the Invention

Mitoxantrone (Mitox), an antitumor 1,4-bis(aminoalkylamino)anthracene-9,10-dione, is currently gaining an important place in the clinical management of leukemias and lymphomas as well as in combination therapy of advanced breast and ovarian cancers. Although Mitox is endowed with an improved tolerability profile compared with doxorubicin (DX) and other anthracyclines, this drug is not devoid of significant toxic side effects, especially those associated with myelosuppression and cardiotoxicity. In particular, congestive heart failure is a serious clinical concern in patients previously treated with anthracyclines (for a recent review on the therapeutic and toxicological profile of mitoxantrone see: Faulds, D.; Balfour, J. A.; Chrisp, P.; Langtry, H. D. "Mitoxantrone, a Review of its Pharmacodynamic and Pharmacokinetic Properties, and Therapeutic Potential in the Chemotherapy of Cancer", *Drugs* 1991, 41, 400–449).

The mechanisms for cellular destruction of Mitox are probably multimodal in their nature: many studies suggest intercalation into DNA as a major cellular event. Nucleic acid compaction and interference with DNA-Topoisomerase II activity, resulting in protein associated-DNA strand breaks have been also proposed as critical events which lead to Mitox induced cell death. Cellular destruction by antitumor anthracene-9,10-diones, including Mitox, has also been attributed to oxidative metabolism which results in the formation of free radicals capable of DNA alkylation and/or DNA scission, yielding non-protein-associated DNA strand breaks. However, it is generally believed that redox-cycling of the quinone moiety is probably more related to the cardiotoxic side effects of Mitox than to the mechanism of its antitumor activity. The cardiotoxicity of Mitox and DX has also been associated with the metal chelating ability of the adjacent hydroxyl and quinone groups. Formation of drug-metal complexes could enhance oxidation-reduction cycling by a metal catalyzed type reaction (Shipp, N. G.; Dorr, R. T.; Alberts, D. S.; Dawson, B. V.; Hendrix, M. "Characterization of experimental mitoxantrone cardiotoxicity and its partial inhibition by ICRF-187 in cultured neonatal rat heart cells", *Canner Res.* 1993, 53, 550–556).

The significant clinical activity of Mitox makes the development of second generation anthracenedione congeners an attractive area of investigation. To date, much research has been devoted to the exploration of variations in the nature of the side-chains and to the repositioning of the hydroxy substituents and/or the lateral side-chains.

The introduction of heteroatoms in the anthraquinone chromophore is a relatively unexplored approach, but such a change could significantly affect the interaction of the molecules with biological targets. In particular, heterocyclic analogues of anthraquinones a) should basically retain the same spatial and planar characteristics as the parent drugs for host molecular recognition such as DNA intercalation, and b) might introduce additional hydrogen bonding or basic sites, either of which could increase the affinity of the drug for DNA and/or affect the interaction with Topoisomerase II. In addition, the heteroanalogues could be endowed with altered redox properties.

Several aza analogues have been prepared and screened (Krapcho, A. P., "6,9-bis(substituted-amino)benzo[g]isoquinoline-5,10-diones. PCT Intl. Appl. WO 92/15300, Sep. 17, 1992 (herein incorporated by reference); A. P. Krapcho et al.: "6,9-bis[(2-aminoalkyl)aminobenzo[g]isoquinoline-5,10-diones. A novel class of chromophore-modified antitumor anthracene- 9,10-diones: synthesis and antitumor evaluation; *J. Med. Chem.* (1994), in press (herein incorporated by reference).

Among these compounds 6,9-bis[(2-aminoethyl)amino]benzo[g]isoquinoline-5,10 dione dimaleate salt emerged as the most active in antitumor experimental models.

6,9-bis[(2-aminoethyl)amino]benzo[g]isoquinoline-5,10-dione dimaleate salt moreover is devoid of any significant toxic effect on cardiac tissue, after both single and multiple treatment, respectively in the rat and mouse. After single treatment in rat with doses approximately equal to $LD_{10}$ and $LD_{50}$, the compound 6,9-bis[(2-aminoethyl)amino]benzo[g]isoquinoline-5,10-dione dimaleate salt induced less erythropenia and thrombocytopenia than Mitox. This favorable profile was confirmed in mice after repeated treatments in comparison with Mitoxantrone at equiactive doses on murine leukemia models.

Unfortunately chemical development of the compound faced unexpected problems due to the low level of purity of the compound (purity as low as 96%). Analytical development of the compound moreover revealed the presence of unknown impurities which are formed during the last step of the preparative process and which cannot be removed from the compound with any currently available purification method. Since the unknown impurities account for more than 2%, and one of these unknown impurities alone accounts for 1.3%, the development of the compound is seriously endangered since regulatory authorities require extensive investigations on unknown impurities if these latter are present in such a significant amount.

SUMMARY OF THE INVENTION

Applicants have discovered new improved methods of synthesis for 6,9-bis[(2-aminoethyl)amino]benzo[g]isoquinoline-5,10-dione and its dimaleate salt. By the new improved methods of synthesis of the invention, this compound can be obtained with greater than 99% purity.

SYNTHESIS OF THE COMPOUND OF THE INVENTION

The compound of the invention, 6,9-bis[(2-aminoethyl)amino]benzo[g]isoquinoline-5,10-dione or its dimaleate salt, is made by two improved methods which result in the production of the compound in very high purity.

Figure 1:
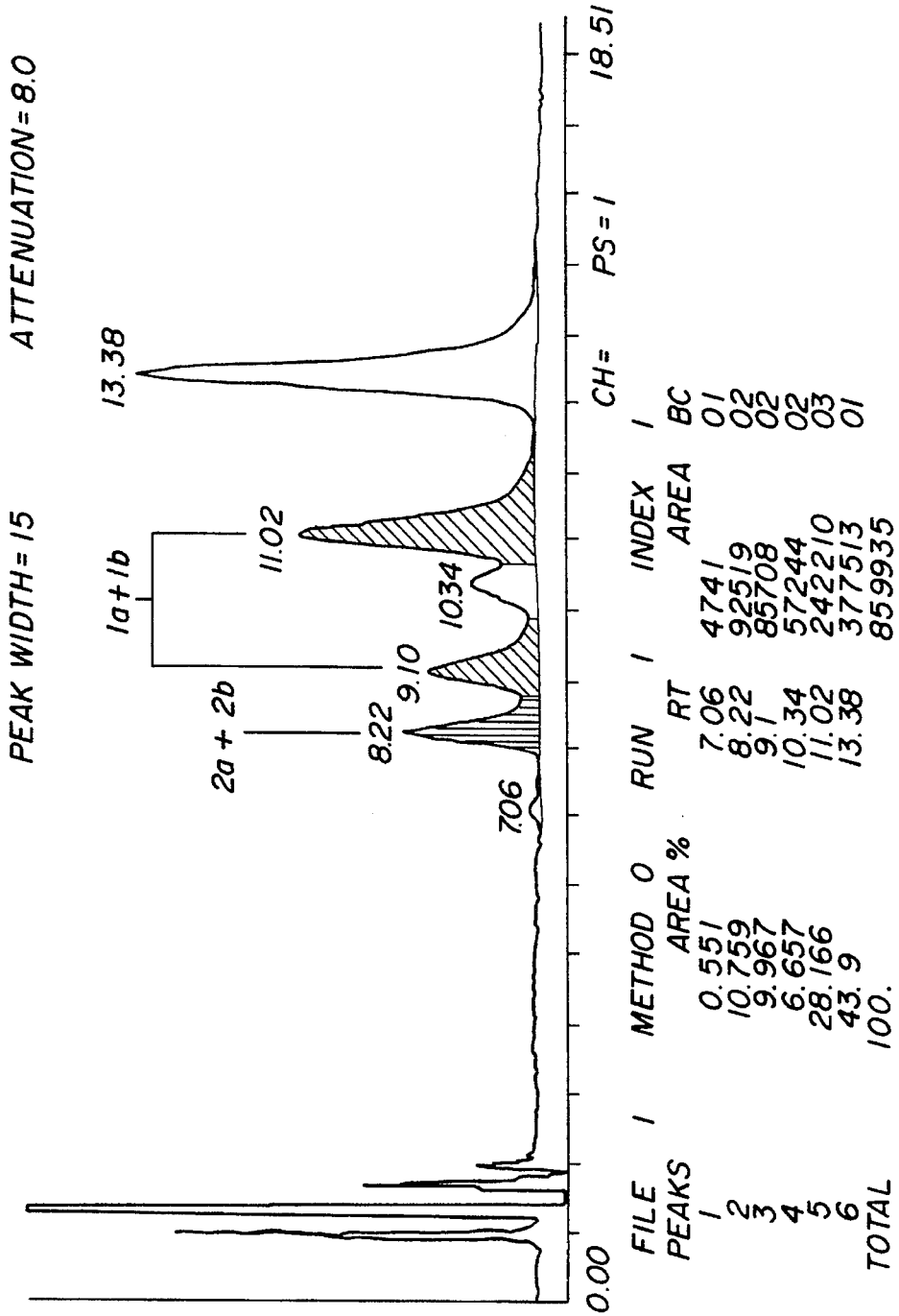
FIG. 1: HPLC analysis reporting a mixture of the compound of the invention, peak 6, and the identified impurities.

The 6,9-bis[(2-aminoethyl)amino]benzo[g]isoquinoline-5,10-dione as free base is not stable because it cyclizes very rapidly in solution leading to compounds 1a and 1b which in HPLC form two different peaks due to either compound (cfr FIG. 1).

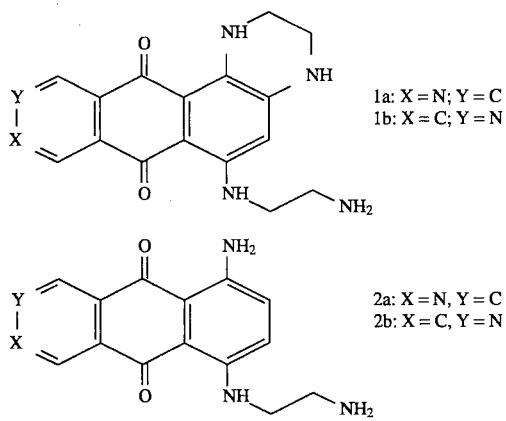

1a: X = N; Y = C
1b: X = C; Y = N

2a: X = N, Y = C
2b: X = C, Y = N

Furthermore, the free base is very soluble in water; therefore, it can hardly be extracted with organic solvents and it is very difficult to be handled and purified.

Moreover, other salts of 6,9-bis[(2-aminoethyl)amino]benzo[g]isoquinoline-5,10-dione, such as the dihydrochloride salt, decompose on standing because they are intrinsically too acidic. In fact, the compound 6,9-bis[(2-aminoethyl)amino]benzo[g]iso-quinoline-5,10-dione at acidic pH (lower than 2.5) decomposes forming compounds 2a and 2b where one side chain is lost. Compounds 2a and 2b are indistinguishable in HPLC and form a single peak (cfr FIG. 1). All of the above reported decomposition products are present as impurities in 6,9-bis[(2-aminoethyl)amino] benzo [g]isoquinoline-5,10-dione (cfr FIG. 2 peaks 3, 4 and 5). The dimaleate salt on the contrary is endowed with an excellent intrinsic stability.

The prior art methods which report on the synthesis of 6,9-bis[(2-aminoethyl)amino]benzo[g]isoquinoline-5,10-dione and of its dimaleate salt are reported in:

1) WO 92/15300 and 2) A. P. Krapcho et al. "6,9-bis[(2-aminoalkyl)amino] benzo[g]isoquinoline-5,10-diones. A novel class of chromophore-modified antitumor anthracene-9,10-diones: synthesis and antitumor evaluations", J. Med. Chem. (1994), in press.

The reported synthetic procedures use, as a key intermediate, 6,9-difluorobenzo[g]isoquinoline-5,10-dione. This compound is reacted with ethylene-diamine which produces the desired 6,9-bis[(2-aminoethyl)amino]benzo[g]isoquinoline-5,10-dione.

Another method is reported involving the reaction of 6,9-difluorobenzo[g]isoquinoline-5,10-dione with mono-t-butoxycarbonyl-ethylene-diamine (BOC-ethylene-diamine) and subsequent removal of the protecting BOC group with dry HCl leading to 6,9-bis[(2-aminoethyl)amino] benzo[g] isoquinoline-5,10-dione dihydrochloride salt. The conversion of the HCl salt into the stable dimaleate salt is not feasible because HCl does not exchange with the less acidic maleic acid. Moreover, the HCl salt, once dissolved in water, decomposes.

Figure 2:
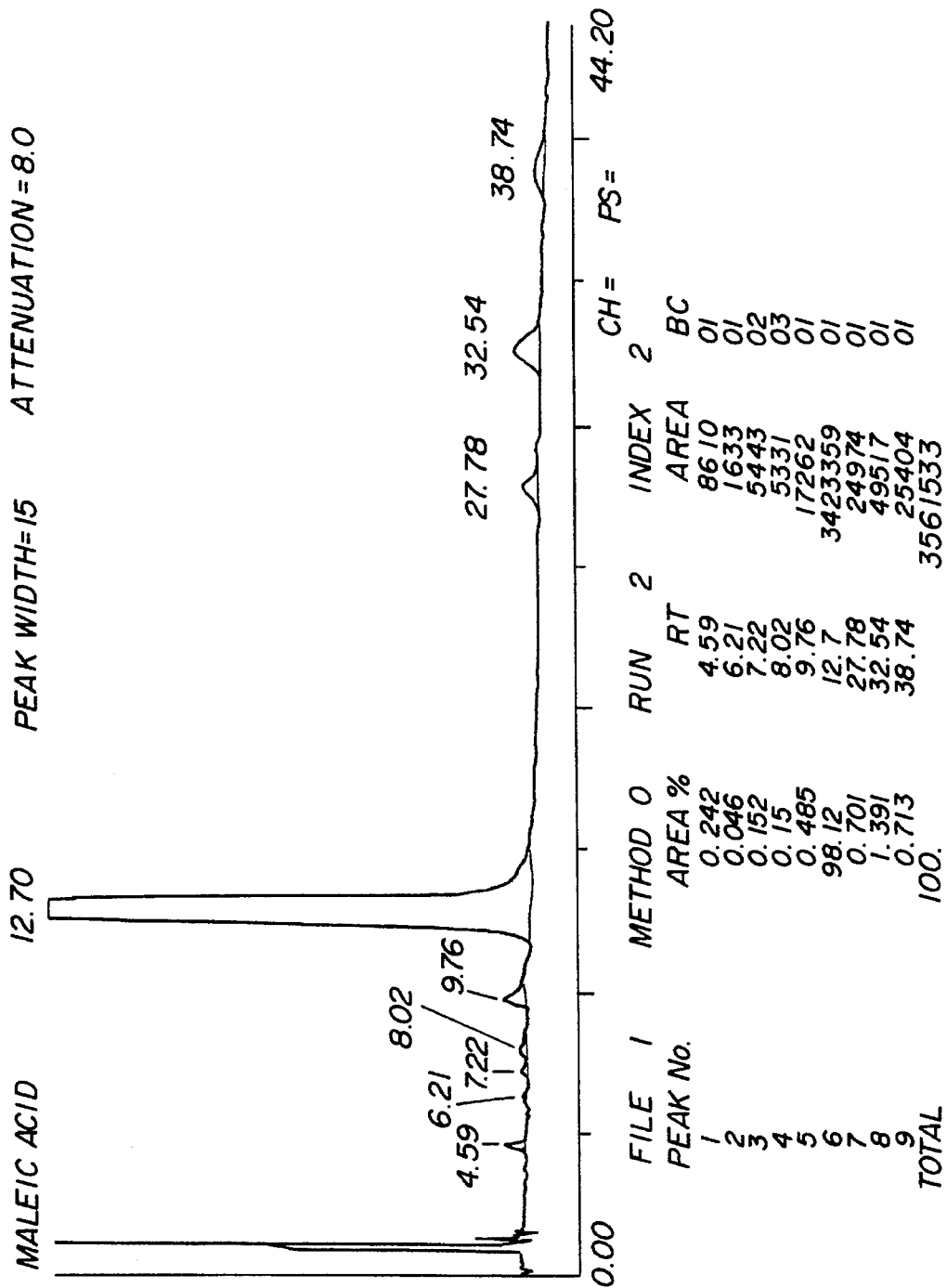
FIG. 2: HPLC analysis of an actual sample of the compound of the invention made by prior art *J. Med. Chem.* or WO 92/15300 method for bis-maleate. The peaks at long retention times, peaks 7, 8, and 9, are unknown impurities.

Moreover, the prior art synthetic methods 1) do not lead to the preparation of 6,9-bis[(2-aminoethyl)amino]benzo[g]iso-quinoline-5,10-dione or its dimaleate salt with a purity higher than 96.1%, and 2) do not avoid the presence of unidentified impurities which are formed during the last step of the process. FIG. 2 reports the HPLC analysis of a typical batch of 6,9-bis[(2-aminoethyl)amino]benzo[g]isoquinoline-5,10-dione dimaleate salt prepared according to the prior art procedure: three unknown impurities are present (cfr peaks 7, 8 and 9) which account for more than 2% and among which one of them (i.e. peak 8) is about 1.3%. The purity of the compound could not be increased and the presence of unknown impurities could not be avoided:

by repeated suspension or crystallization in different solvents or mixtures of solvents since the amount of unknown impurities remains constant,
by column chromatography
or by performing the last step of the synthetic procedure in different solvents and at different temperatures.

Moreover, according to the prior art methods, during the work-up of the last step the precipitation of the compound as dimaleate salt is obtained in the presence of a suspension of the crude dihydrofluoride. A complete solution is never achieved. In the scale-up of the process, this suspension might lead to a nonhomogenous product which could trap other salts and/or contain undesired materials (i.e., insoluble materials, impurities). The complete dissolution of the final product, at least once during the final step, is an important prerequisite for obtaining a chemical compound which is intended for use in mammalian therapy.

These drawbacks typical of the prior art synthetic procedures constitute a serious obstacle for the production and development of the compound of the invention. Regulatory authorities do not usually allow the introduction to human treatments of drugs with the active principle ingredient with a purity as low as 96%, particularly if unknown impurities accounting for more than 2% are present. It is highly preferable to avoid the presence of any impurity present in amounts higher than 0.5%.

We now surprisingly provide new processes which allow one to obtain 6,9-bis[(2-aminoethyl)amino]benzo[g]isoquinoline-5,10-dione and its dimaleate salt with a purity superior to 97%, and preferably greater than 99%, with each of the contained impurities present in amounts lower than 0.5%, and with each of the unknown impurities lower than 0.2%, i.e., at the limit of detection of the analytical method.

The formation of 6,9-bis[(2-aminoethyl)amino]benzo[g]iso-quinoline-5,10-dione and of its dimaleate salt can be accomplished by using either of the following processes:

Process A: Including the following new characteristics:
the reaction of 6,9-bis[(2-aminoethyl)amino]benzo[g]iso-quinoline-5,10-dione with ethylene-diamine is performed by inverse addition i.e., by slowly adding the solid 6,9-difluorobenzo[ g]isoquinoline-5,10-dione to a solution of a large excess of the diamine in THF.
the crude dihydrofluoride of 6,9-bis[(2-aminoethyl)amino] benzo[g]isoquinoline-5,10-dione obtained from the reaction mixture is completely dissolved in water and acetic acid at pH=5; the solution is then filtered and from above solution the dimaleate salt is crystallized by adding a solution of maleic acid in water.

The inverse addition and the rate of the addition itself are critical for the high purity of the product and allows to obtain very high yields (92%). Also very important is the selection of the solvent: the use of THF instead of pyridine improves the yield. The dissolution of the crude dihydrofluoride is important for the high purity and homogeneity of the final product. Moreover, the pH at which the dissolution is performed is critical in order to avoid the formation of other undesired impurities. The complete procedure is described in Example 1, below.

Process B: Including the following new characteristics:

the intermediate 6,9-difluorobenzo[g]isoquinoline-5,10-dione is reacted with mono-BOC-ethylenediamine and the resulting intermediate 6,9-bis[2[[N(t-butoxycarbonyl)amino]ethyl]amino]benzo[g]isoquinoline-5,10-dione is treated with trifluoroacetic acid leading to the crude 6,9-bis[(2-aminoethyl)amino]benzo [g]isoquinoline-5,10-dione trifluoroacetate salt which is then completely dissolved in water, the pH adjusted to 4.2 with NaOH, and filtered;

the above solution of the crude trifluoroacetate salt is treated with an aqueous solution of maleic acid leading to the crystallization of the pure 6,9-bis[(2-aminoethyl) amino] benzo[g]isoquinoline-5,10-dione dimaleate salt.

The complete procedure is described in Example 4, below.

We have surprisingly discovered that the desired 6,9-bis[(2-aminoethyl)amino]benzo[g]isoquinoline-5,10-dione dimaleate can be obtained by displacement of the corresponding crude trifluoroacetate which can be obtained by removal of BOC-protecting groups with trifluoroacetic acid.

The preparation of the key intermediate 6,9-difluorobenzo[ g]isoquinoline-5,10-dione can be accomplished by a multi-step improved procedure. The improvements have been introduced in order to increase the yields and in order to allow the scale-up of the process which is essential for the pharmaceutical development of the 6,9-bis[(2-aminoethyl)amino] benzo[g]isoquinoline-5,10-dione.

The reaction of 1,4-difluorobenzene with pyridine-3,4-dicarboxylic anhydride, in the presence of aluminum chloride leading to a mixture of 4-(2',5'-difluorobenzoyl)nicotinic acid and 3-(2',5'-difluorobenzoyl)isonicotinic acid is conducted as described with the modification that the reaction mixture is diluted with nitrobenzene after recovery of excess 1,4-difluorobenzene and then slowly poured into water. The prior art procedure required the addition of water to the whole semisolid reaction mixture, after recovery of excess 1,4-difluorobenzene: this procedure is extremely risky and not suitable to be reproduced in large scale because of the highly exothermic reaction of aluminum chloride with water. The new work-up allows one to add slowly a solution of the remaining aluminum complexes and excess chloride to a large excess of water.

The resulting mixture of 4-(2',5'-difluorobenzoyl) nicotinic acid and 3-(2',5'-difluorobenzoyl)isonicotinic acid is then subjected to a cyclization reaction in 20% fuming sulfuric acid with the improvement that further portionwise addition of 20% fuming sulfuric acid allows to increase the yields up to 81%.

Preparative Example 1

Preparation of 3,4-Pyridine Dicarboxylic Acid Anhydride

Under nitrogen atmosphere a suspension of a 97% pure 3,4-pyridine dicarboxylic acid (152 g, 0.88 mol) in acetic anhydride (450 mL) was heated to reflux and a complete solution was obtained. Once refluxing temperature was reached, solvent was removed by distillation at atmospheric pressure (about 400 mL were collected) over a period of about 1 hour. Vapors temperature was observed to increase from about 132° C. to 140° C. and distillation was stopped when internal temperature reached 150°–155° C. The reaction mixture was cooled to 70° C. and tert-BuOMe (450 mL) was added dropwise under stirring. A dark grey solid precipitated at about 40° C. while temperature was spontaneously let reach 20°–25° C. The suspension was further cooled to 0°–5° C. and stirred for two hours. Under nitrogen blanket the dark grey precipitate was collected by filtration, washed with tert-BuOMe (100 mL) and dried under vacuum (20 torr; 30° C.; 2 h) to yield 3,4-pyridine dicarboxylic acid anhydride (100 g; yield 76%) which was directly used in the next step.

3,4-Pyridine dicarboxylic acid anhydride is highly sensitive to atmospheric moisture so it must be handled under nitrogen and stored over $P_2O_5$. mp: 72°–74° C.

Preparative Example 2

4-(2',5'-Difluorobenzoyl)nicotinic Acid and 3-(2',5'-difluorobenzoyl) isonicotinic Acid 3,4-Pyridine dicarboxylic acid anhydride (95.7 g, 0.67 mol) and $AlCl_3$ (367.3 g, 2.67 mol) were simultaneously, but separately, added in five portions (one every 15') to boiling 1,4-difluorobenzene (650 mL, 90° C.). After about 1 hour from the last addition, the majority of the 1,4-difluorobenzene was removed by distillation at normal pressure until a thick mass was obtained. The temperature was lowered to 80° C. and nitrobenzene (150 mL) was added in order to dissolve the residual mass. While still hot, the resulting solution was cautiously quenched into ice-cooled and stirred water (1000 g of ice and 530 g of demineralized water) (i.e., slowly drop the solution into the ice water). Then concentrated HCl (37%, 160 mL) was added to the poured mixture at 0°–5° C. and stirring was continued for about 3 hours. A greasy beige precipitate (about 150 g wet) was collected by filtration while the aqueous layer was separated from nitrobenzene and extracted with AcOEt (6×500 mL). Nitrobenzene layer was diluted with petroleum ether (400 mL) and the resulting little amount of precipitate was collected by filtration (about 2 g). Combined extracts were concentrated under vacuum, and the residual crude solid (about 45 g), together with the previously collected precipitates, was suspended into a mixture of AcOEt/petroleum ether (½) (600 mL). After about 2 hours at room temperature the suspension was filtered and dried in vacuum to give the mixture of 4-(2',5'-difluorobenzoyl)nicotinic acid and 3-(2',5'-difluorobenzoyl) isonicotinic acid (147.3 g, 84% yield) as a pale beige solid. mp: 214°–216° C.

Preparative Example 3

6,9-difluorobenzo[g]isoquinoline-5,10-dione

A solution of the mixture of 4-(2',5'-difluorobenzoyl) nicotinic acid and 3-(2',5'-difluorobenzoyl)isonicotinic acid (120 g, 0.456 mol) in fuming 20% $H_2SO_4$ (180 mL) was heated to 140° C. After about 30 minutes, more fuming 20% sulfuric acid (120 mL) was added to the hot reaction mixture in four portions of 30 mL each, every 20 minutes. Twenty minutes after the last addition the reaction mixture was cooled at about 80° C. and then was poured onto iced demineralized water (3000 g of ice and 3000 mL of water). The pH of the quenched reaction mixture was adjusted to 1 with 40% NaOH (850 mL) and the formation of a yellow-brown precipitate was observed. After about 1 hour at 0°–5° C. the crude precipitate was filtered and dried under vacuum to give crude 6,9-difluorobenzo [g]isoquinoline-5,10-dione (98.5 g). The reaction crude was dissolved in boiling THF (1000 mL) and the hot solution was decolored with active charcoal (9 g), filtered and concentrated to a volume of about 300 mL. After cooling at 0°–5° C. for about 2 hours a yellow solid was collected by filtration to afford analytically pure 6,9-difluorobenzo[g]isoquinoline-5,10-dione (90.6 g, 81% yield). mp: 197°–199° C.

Example 1

6,9-bis[(2-aminoethyl)amino]benzo[g]isoquinoline-5,10-dione dimaleate

To a warm solution (55° C.) of ethylenediamine (154.4 mL, 2.29 mol) in THF (1400 mL), 6,9-difluorobenzo[g]isoquinoline-5,10-dione (70.1 g, 0.29 mol) was portionwise added over a period of 2.5 hours (about 4.6 g/10' each portion). The mixture was stirred for 3 hours at the same temperature and a blue precipitate was gradually formed. After one night stirring at 25° C., the suspension was filtered under nitrogen blanket, washed with THF (200 mL) and dried under vacuum (15 torr, 60° C., 3 h) to yield crude 6,9-bis[(2-aminoethyl)amino] benzo[g]isoquinoline-5,10-dione as dihydrofluoride salt (117 g).

The crude product was directly dissolved into a mixture of water (2340 mL) and AcOH (40 mL) in order to obtain a dark blue solution, whose pH was about 5, which was filtered on a glass-fiber filter. This pH value is very important to prevent any degradation of the reaction product. The filtered solution was gradually treated at room temperature with a 3M aqueous filtered solution of maleic acid (585 mL) to reach pH 3.5. After about 30' at 40° C., the suspension was stirred overnight at room temperature. The blue precipitate was filtered and washed with additional water (3×80 mL) and EtOH (3×100 mL) then dried under vacuum (15 torr, 60° C., 4 h) to give crude 6,9-bis[(2-aminoethyl)amino]benzo[g]iso-quinoline-5,10-dione dimaleate (168 g).

The crude dimaleate salt was suspended in water (3180 mL) and heated to 50° C. for 30'. After one night stirring at 25° C., the suspension was filtered again, the blue precipitate was washed with additional water (3×100 mL) and this moist material was resuspended in water (2400 mL) and kept under stirring at room temperature for about 40 h.

The dimaleate salt was filtered, washed with additional water, (3×100 mL) and EtOH (3×100 mL) and then dried under vacuum (15 torr, 60° C., 4 h, then 40° C., one night) to yield 6,9-bis[ (2-aminoethyl)amino]benzo[g]isoquinoline-5,10-dione dimaleate (146.7 g, 92% yield).

Figure 3:
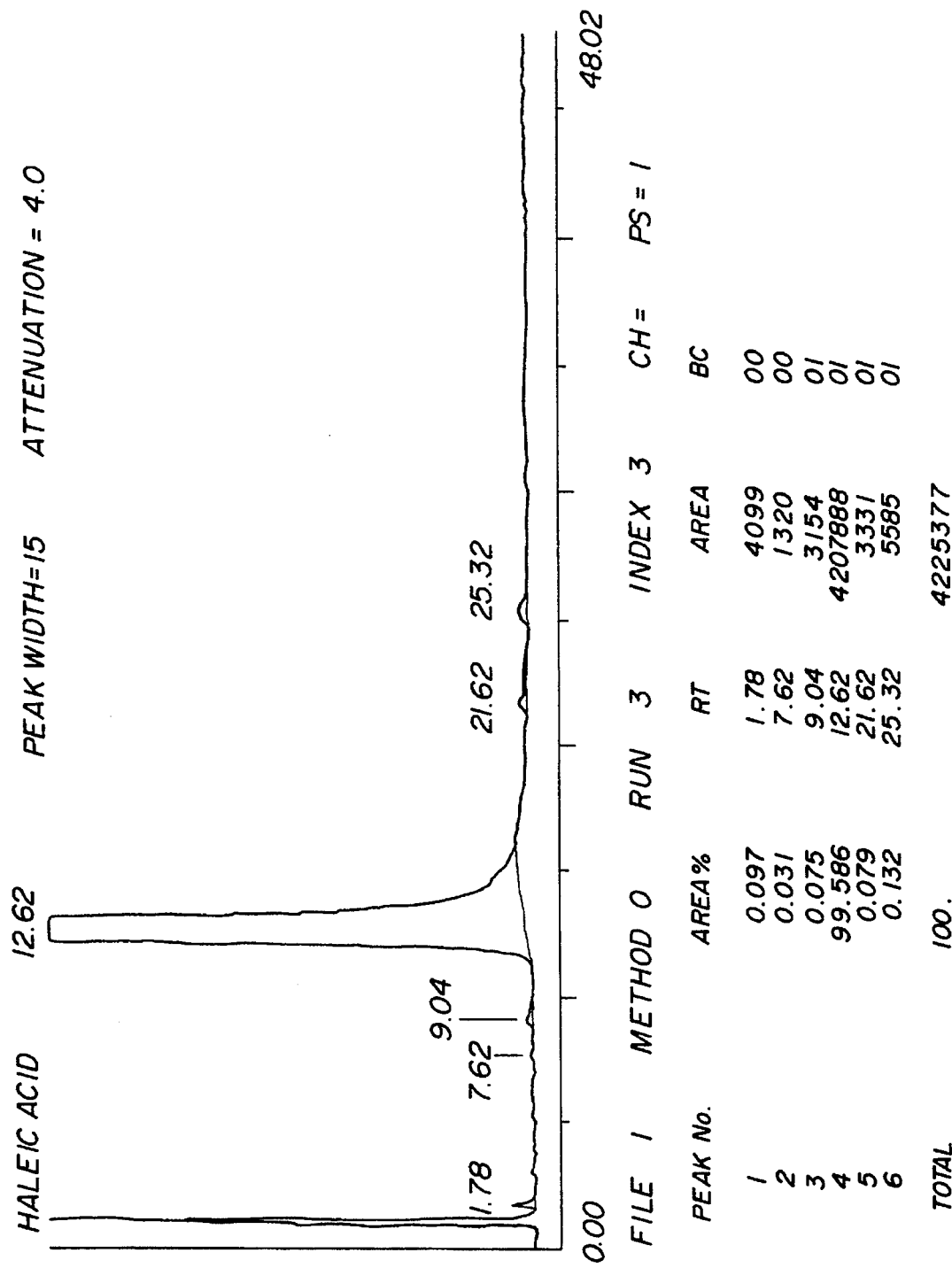
FIG. 3: HPLC analysis of the compound of the invention prepared according to process A of the invention.

HPLC analyses (Waters, UV/Vis detector 486, Pump 510):
column: Lichrospher C18 (5 μm) t.a.
eluent: $H_2O/CH_3CN$/dioxane 75/20/5 Sodium heptane sulfonate (20 mMol) pH 3.0 with $H_3PO_4$
flow rate: 1 mL/min
detector: UV (245 nm)
r.t.: 12 min
HPLC purity (area %)=99.586%; cfr FIG. 3, peak n° 4
$^1$H-NMR analyses (Brucker 200 MHz spectrometer, chemical shifts (δ) are reported in parts per million downfield from the internal standard $Me_4Si$).

(δ; $D_2O$): 3.30 (m, 4H); 3.70 (m, 4H); 6.05 (s, 4H); 7.05 (s, 2H); 7.70 (d, 1H); 8.70 (d, 1H); 8.95 (s, 1H).

Example 2

Under nitrogen atmosphere a solution of di-t-butyl dicarbonate (290.8 g, 1.32 mol) in dry THF (1200 mL) was slowly added over a period of about 3 h to a cooled (0° C.) and stirred solution of 1,2-ethylene-diamine (268 mL, 4 mol) in THF (3600 mL). After 3 hours at 10° C. and about 16 hours at room temperature, the solvent was removed under vacuum. The residual yellow oil (about 230 g) was dissolved in isopropylether (460 mL) and washed with brine (50 mL). After drying over sodium sulfate (50 g) the organic solution was concentrated to a small volume and distilled under reduced pressure (8 torr, 119°–121° C.) to yield N-t-butoxycarbonyl- 1,2-ethylene-diamine (161 g, 76% yield respect to di-t-butyldicarbonate). NMR ($CDCL_3$, δ) 1.3 (s, 2H, exchanges with $D_2O$), 1.4 (s, 9H), 2.7 (bt, 2H), 3.1 (dd, 2H), 5.4 (bs, 1H)

Example 3

Under nitrogen a solution of 6,9-difluorobenzo[g]isoquinoline-5,10-dione (15 g, 0.061 mol) and N-t-butoxycarbonyl-1,2-ethylenediamine (49 g, 0.305 mol) in anhydrous N-methylpyrrolidone (300 mL) was heated to 60° C. After about 4.5 hours, the reaction mixture was slightly cooled (50° C.) and poured into stirred demineralized water (1500 mL). Stirring was continued for 2 hours at room temperature and the dark blue precipitate solid was collected by filtration and washed with water. The crude filtered precipitate was resuspended in water (1500 mL), filtered and dried under vacuum. The reaction crude was dissolved into a hot mixture of methylene chloride and methanol (¹/₁, 500 mL), the warm solution was filtered on a glass-fiber filter and cooled to 10°–15° C. for two hours. After further 16 hours at room temperature the dark blue crystallized product was collected by filtration and dried to give 27 g of 6,9-bis-[(2-N-t-butoxycarbonylaminoethyl)amino]benzo[g] isoquinoline-5, 10-dione (84% yield).

NMR ($CDCl_3$, δ): 1.4 (s, 18H), 3.4–3.7 (m, 8H), 5.4 (m, 2H), 7.3 (s, 2H), 8 (d, J=6 Hz, 1H), 8.85 (d, J=6 Hz, 1H), 9.5 (s, 1H), 11 (m, 2H)

Example 4

Trifluoroacetic acid (32 mL, 0.42 mol) was added to a suspension of 6,9-bis-[(2-N-tert-butoxycarbonylamino ethyl)amino] benzo[g]isoquinoline-5,10-dione (22 g, 0.042 mol) in methylene chloride (330 mL). After stirring for about 16 hours at room temperature, the reaction mixture was diluted with EtOH (100 mL) and concentrated under vacuum. The residual oil was newly diluted with ethanol (300 mL) and concentrated again to a small volume. The demineralized water (220 mL) was added to the oily residue and pH was adjusted to 4.2 units with aqueous 20% KOH (45 mL). The obtained dark blue solution was filtered on a glass-fiber filter and mixed with an aqueous 3M solution of maleic acid (45 mL, 0.135 mol). The pH of the solution was readjusted to 3.4 units with 20% KOH (24 mL) and the mixture was stirred at room temperature for about 40 hours. The crude maleate was collected by filtration and resuspended in demineralized water (200 mL), warmed to 50° C. for 1 hour and kept under stirring for additional 16 hours at room temperature. A dark blue solid was filtered, washed with water (2×50 mL) and ethanol (2×50 mL) and dried under vacuum to yield 18.6 g of 6,9-bis[(2-aminoethyl)amino]benzo[g]isoquinoline-5,10-dione dimaleate salt (80% yield).

Figure 4:
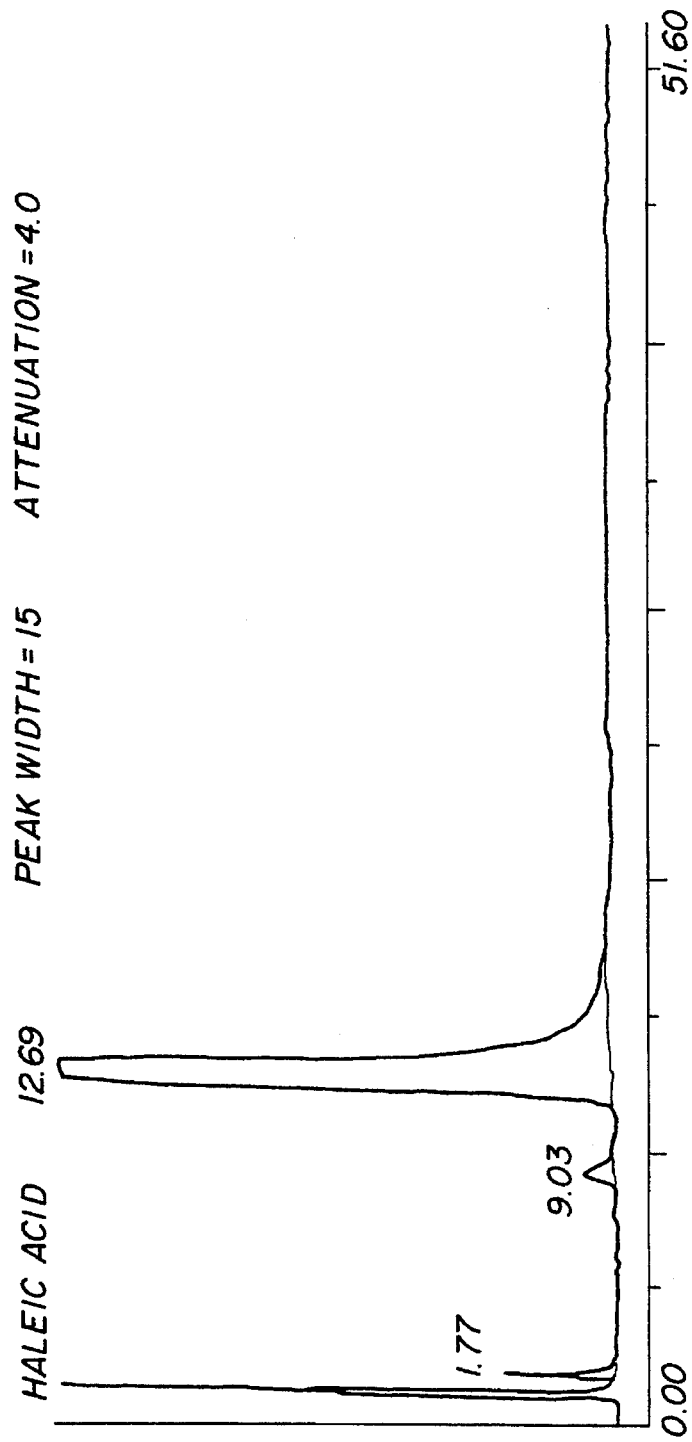
FIG. 4: HPLC analysis of the compound of the invention prepared according to process B of the invention.

HPLC analyses (Waters, UV/Vis detector 486, Pump 510):
column: Lichrospher C18 (5 μm) t.a.
eluent: $H_2O/CH_3CN$/dioxane 75/20/5 Sodium heptane sulfonate (20 mMol) pH 3.0 with $H_3PO_4$
flow rate: 1 mL/min
detector: UV (245 nm)
r.t.: 12 min
HPLC purity (area %)=99,285%; cfr FIG. 4, peak n° 3

$^1$H-NMR analyses (Brucker 200 MHz spectrometer, chemical shifts (δ) are reported in parts per million downfield from the internal standard Me$_4$Si).

(δ; D$_2$O): 3.30 (m, 4H); 3.70 (m, 4H); 6.05 (s, 4H); 7.05 (s, 2H); 7.70 (d, 1H); 8.70 (d, 1H); 8.95 (s, 1H).

TREATMENT

The compound of the present invention may be used as active ingredient of therapeutic compositions to induce regression and/or palliation of cancers in mammals when administered in amounts ranging from about 1 mg to about 0.4 g/kilogram of body weight. A preferred dosage regimen would be from about 1 mg to about 50 mg per kilogram of body weight per day. Unit dosage may be employed so that from about 70 mg to about 3.5 g of the active compound for a subject of about 70 kg of body weight are administered in a 24 hour period. The dosage may be adjusted to be compatible to other treatment regimens, such as radiation therapy.

The pharmaceutical compositions may be in the form of tablets, capsules, gel capsules, suppositories, lyophilized powders, and solutions for intravenous administration.

We claim:

1. The compound 6,9-bis[(2-aminoethyl)amino] benzo[g] isoquinoline-5,10-dione or a physiologically acceptable salt thereof with a purity greater than 99%.

2. A pharmaceutical composition comprising the compound of claim 1 and a pharmaceutically acceptable excipient.

3. The compound of claim 1 wherein none of the contained impurities exceeds 0.5%.

4. The compound of claim 1 wherein none of the unknown contained impurities exceeds 0.2%.

5. The compound of claim 1 as a dimaleate salt.

* * * * *